(12) United States Patent
Jalali

(10) Patent No.: US 9,636,425 B2
(45) Date of Patent: May 2, 2017

(54) METHOD OF DRY DYE DELIVERY FOR STAINING THE EYE

(71) Applicant: Amir Sahba Jalali, Columbia, MO (US)

(72) Inventor: Amir Sahba Jalali, Columbia, MO (US)

(73) Assignee: Focal Point Technologies, LLC, Columbia, MO (US)

( * ) Notice: Subject to any disclaimer, the term of this patent is extended or adjusted under 35 U.S.C. 154(b) by 781 days.

(21) Appl. No.: 13/622,229

(22) Filed: Sep. 18, 2012

(65) Prior Publication Data

US 2014/0081168 A1    Mar. 20, 2014

(51) Int. Cl.
| A61B 10/00 | (2006.01) |
| A61B 5/00 | (2006.01) |
| A61B 8/00 | (2006.01) |
| A61K 49/00 | (2006.01) |
| A61K 9/00 | (2006.01) |

(52) U.S. Cl.
CPC ........ A61K 49/006 (2013.01); A61K 49/0043 (2013.01); *A61K 9/0048* (2013.01)

(58) Field of Classification Search
CPC .. A61K 49/00; A61K 49/0043; A61K 49/006; A61K 49/0032; A61K 49/0056; A61K 49/0021; A61K 41/0057; A61K 41/0033; A61K 9/00; A61K 9/0048
USPC .......................... 424/1.11, 1.65, 9.1, 9.2, 9.6
See application file for complete search history.

(56) References Cited

U.S. PATENT DOCUMENTS

| 5,510,339 | A | * | 4/1996 | Gleich | ................. A61K 31/165 514/171 |
| 6,547,770 | B2 | * | 4/2003 | Carlsson et al. | .............. 604/294 |
| 7,281,801 | B2 | * | 10/2007 | Wang | ..................... A61B 3/101 351/205 |
| 2003/0211043 | A1 | * | 11/2003 | Korb | ................... A61K 9/0048 424/9.6 |
| 2009/0130024 | A1 | * | 5/2009 | Narayanan et al. | ........... 424/9.6 |
| 2014/0373832 | A1 | * | 12/2014 | Zeng | ....................... A61K 9/12 128/200.23 |

* cited by examiner

*Primary Examiner* — D L Jones
(74) *Attorney, Agent, or Firm* — Lathrop & Gage, LLP; Alan W. Steele

(57) ABSTRACT

A device and method for staining the eye of a patient in need of the same includes the introduction, onto the surface of the eye, of a dry powder form at a dye suitable for staining the eye. The dry powder form of the dye is introduced onto the surface of the eye without the use of a substrate at or near the eye's surface.

5 Claims, 4 Drawing Sheets

METHOD OF DRY DYE DELIVERY FOR STAINING THE EYE

RELATED APPLICATIONS

Not Applicable.

BACKGROUND OF THE INVENTION

1. Field of the Invention

The present invention relates generally to a method of staining the surface of the eye, and more specifically to a method of staining the surface of the eye with a dry dye introduced directly onto the surface of the eye.

2. Background

Physicians regularly employ staining of the surface of the eye to aid in the diagnosis of various eye conditions. Dyes used for this purpose include Fluorescein, Lissamine Green, and Rose Bengal. Staining can aid in the diagnosis of corneal abrasion, infection, injury or trauma to the eye, foreign bodies in the eye, abnormal tear production, and dry eye, including severe dry eye such as keratoconjunctivitis sicca. Proper diagnosis of an eye condition aids the physician in selecting the appropriate treatment.

Dry eye disease is one of the most common conditions encountered by primary eye care physicians. Fluorescein staining is considered one of the most valuable tests in diagnosing dry eye disease. Typically, a length of filter paper or other substrate impregnated with Fluorescein dye is touched to the surface of the eye, allowing the dye to be introduced onto the cornea. Blinking by the patient spreads the dye, which readily diffuses into the tear film of the eye. The dye is then generally visualized under a cobalt blue lamp. The integrity of the tear film can be assessed by measuring the tear-film break up time while the eye is under the cobalt blue light. Further, corneal staining by the dye can indicate corneal injury, secondary to dry eye or due to other causes, as well as localized depressions in the eye resulting from prolonged dryness. The level of staining visualized under the cobalt blue lamp is indicative of the severity of the condition.

Lissamine Green and Rose Bengal are also used to diagnose eye conditions, including dry eye. These dyes are useful in detecting dead or devitalized cells on the corneal surface, as well as on the conjunctiva. Introduction of these dyes into the eye of a patient is performed in the same manner as the introduction of Fluorescein.

While the dyes described above, as well as others, are valuable in diagnosing disorders of the eye, the method of introduction of the dye into the eye can be problematic. Because the filter paper or other substrate used is contacted directly with the surface of the eye, there is a risk of introduction of bacteria onto the eye surface. Further, the substrate is often made wet with saline solution prior to introduction onto the eye, increasing the chance of introducing microorganisms onto the eye if the saline solution is not properly sterile. Use of a substrate such as filter paper can also abrade the cornea or conjunctiva of the eye. These risks are associated with the introduction of any physical object onto the surface of the eye. In some cases, liquid drops containing dye may be used to avoid contact with the eye. Such liquids, however, are susceptible to bacterial growth and as such still carry the risk of infection.

SUMMARY OF THE INVENTION

The present invention provides a method of staining the eye of a patient in need of the same. The method includes the introduction, onto the surface of the eye, of a dry powder form of a dye suitable for staining the eye. The dry powder form of the dye is introduced onto the surface of the eye without the use of a substrate at or near the eye's surface.

In another aspect of the present invention, the amount of dry powder dye used for staining the eye ranges from about 0.001 mg to about 1 mg.

In another aspect of the invention, the dry powder dye is selected from the group consisting of Fluorescein, Lissamine Green, Rose Bengal, and combinations thereof.

In another aspect of the invention, the dry powder form of the dye is introduced onto the surface of the eye by force of gravity alone.

In another aspect of the invention, a device is used to introduce a small, measured amount of the dry powder dye onto the surface of the eye.

In still another aspect of the invention, the device used to introduced the dry powder dye onto the surface of the eye utilizes compressed gas.

Another aspect of the present invention provides a method for staining the eye of a patient in need thereof without contacting the surface of the eye with a physical object to deliver the dye. The method includes the step of providing a delivery device including a sealed container, an actuator, a dry dye formulation within the delivery device, and a propellant under pressure within the delivery device. The user of the device engages the actuator to dispense the dye from the device.

In another aspect of the invention, the actuator is metered such that a single engagement of the actuator dispenses a predetermined amount of dye.

Another aspect of the invention provides a device for delivering a dry dye formulation. The device includes a sealed container, a propellant within the sealed container, a dry dye formulation within the sealed container, and a valve. The user of the device opens the valve to dispense the dye.

In another aspect of the invention, the device includes an actuator for opening the valve.

In another aspect of the invention, the device includes a meter such that a single actuation of the device dispenses a predetermined amount of dye.

DETAILED DESCRIPTION OF THE INVENTION

Figure 1:
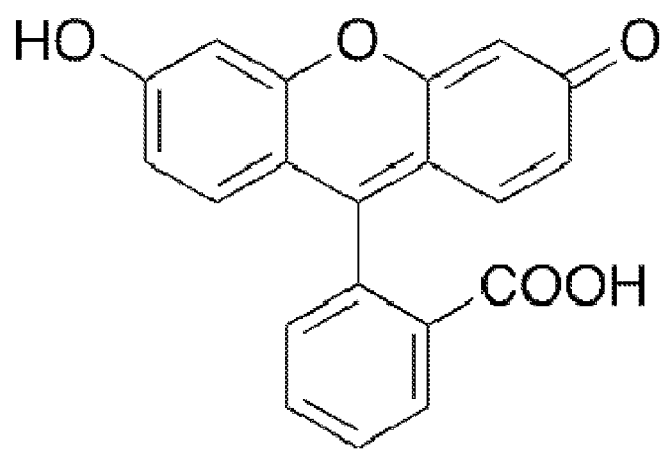
FIG. 1 provides the chemical structure of Fluorescein.

FIG. 1 illustrates the structure of Fluorescein, a dye commonly used to stain the surface of the eye, having a molecular formula $C_{20}H_{12}O_5$. The dye is generally provided in a powder form, and is soluble in water or alcohol. Generally, the sodium salt of Fluorescein is used for staining the eye. The dye has maximum absorption at around 494 nanometers, which renders it highly absorptive of blue light. A cobalt blue light is generally used to visualize Fluorescein on the surface of the eye.

Figure 2:
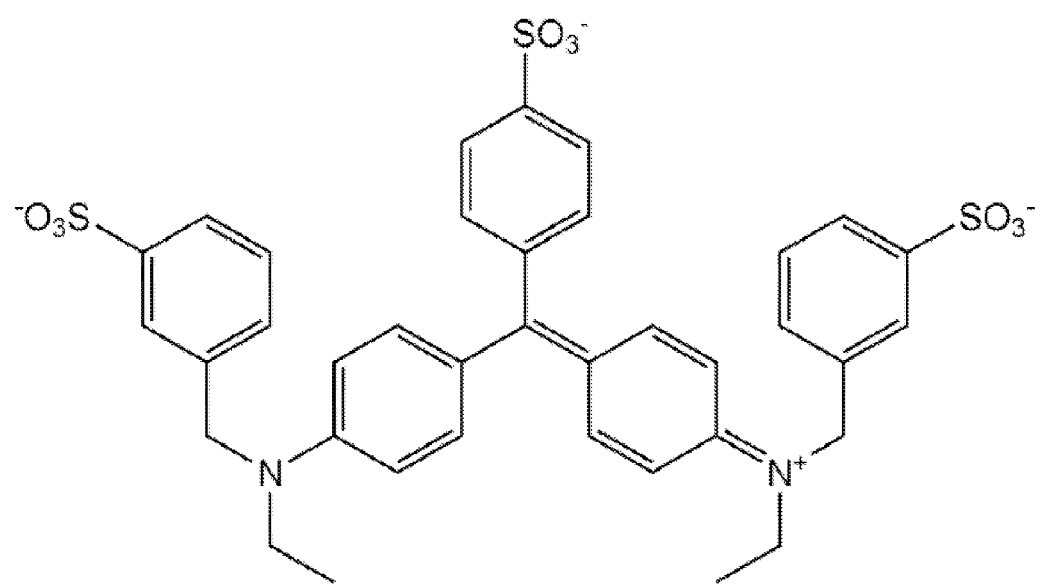
FIG. 2 provides the chemical structure of Lissamine Green.

Lissamine Green is a triarylmethane dye having a molecular formula $C_{37}H_{37}N_2O_9S_3$. The structure of the dye is provided in FIG. 2. Lissamine Green is generally provided as a disodium salt and has maximum absorption at 630 and 422 nanometers. The dye is generally visualized with a blue or white light.

Figure 3:
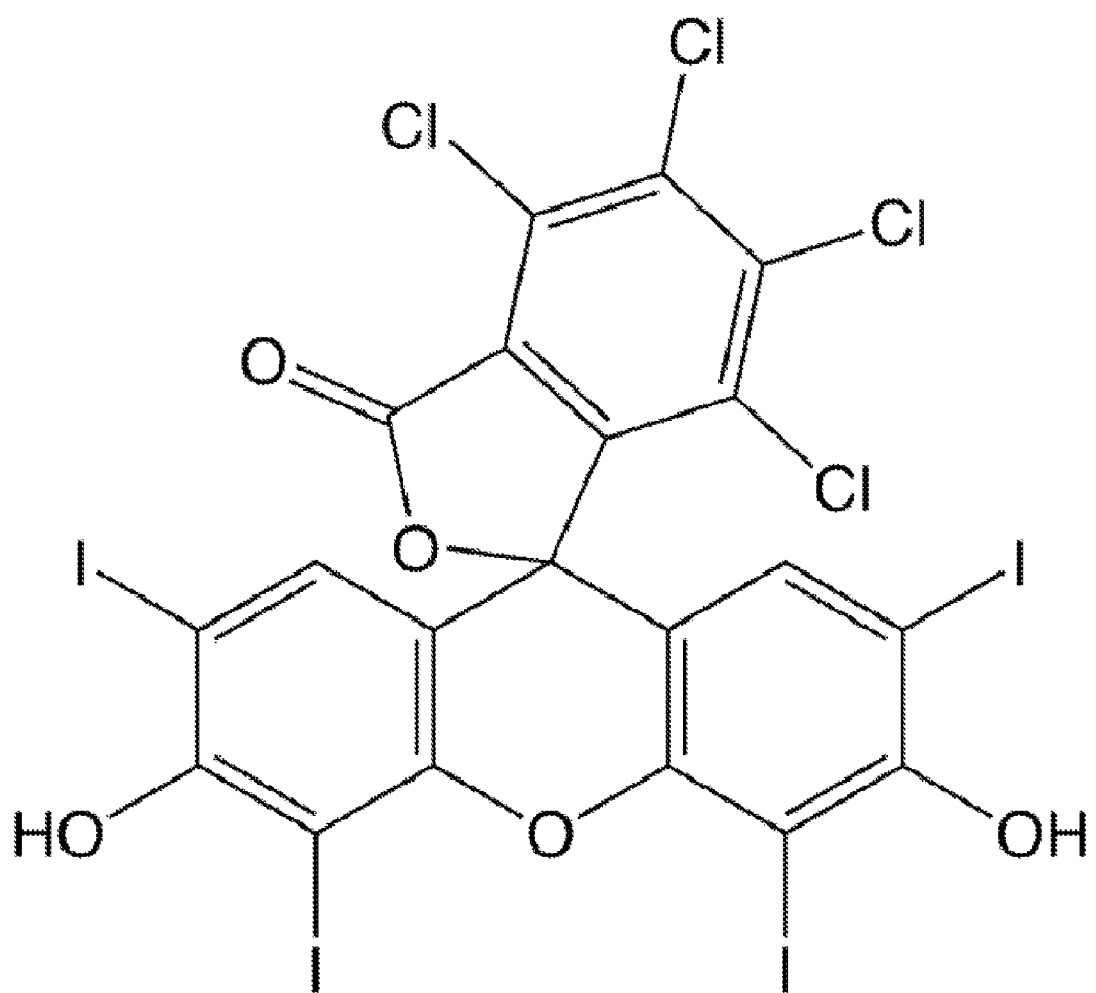
FIG. 3 provides the chemical structure of Rose Bengal.

Rose Bengal is a Fluorescein derivative having a molecular formula $C_{20}H_4Cl_4I_4O_5$. The structure of Rose Bengal is provided in FIG. 3. The sodium salt of Rose Bengal is often used to stain damaged conjunctival and corneal cells in the eye.

Although the three dyes described above are referred to specifically in this writing, it should be understood that the principles of the present invention may be utilized with any suitable dye.

The present invention provides a device and method for introducing dry dye onto the surface of the eye of a patient, without the introduction of a physical object, such as filter paper or other substrate, onto the eye's surface. Introduction of the dry dye directly onto the eye without the need for an intermediary substrate or object reduces the risk of infection of the eye, as well as the risk of damage to the eye due to abrading of the cornea or conjunctiva. As used herein, the word "substrate" refers to any physical object or structure carrying the dye, whether the dye is provided on the surface of the substrate or the substrate is impregnated with the dye.

The amount of dry dye required to be introduced onto the surface of the eye may vary according to the specific dye employed. For the dyes mentioned above, it is contemplated that from about 0.001 mg to about 1 mg will be sufficient to stain the cornea and conjunctiva. Any suitable device for delivery of a small quantity of dry powder can be utilized with the teachings of the present invention.

Exemplary devices for delivering the dyes in accordance with the present method may include devices having a reservoir for the powdered dye, as well as a pressurized gas source. The pressurized gas can be utilized to aerosolize the dry powder and direct it to the surface of the eye. Such devices can provide precise delivery of dry medicaments, including delivery of small amounts of fine powder. Production of a device for delivery the appropriate amount of a dye for use with the present method is considered within the skill of those in the art. Further, although a device may be used for delivery of the dye onto the eye's surface, it is contemplated that the dry dye powder can be delivered to the eye through the force of gravity alone, such as by dropping the desired amount of dry powder directly onto the surface of the eye.

Figure 4:
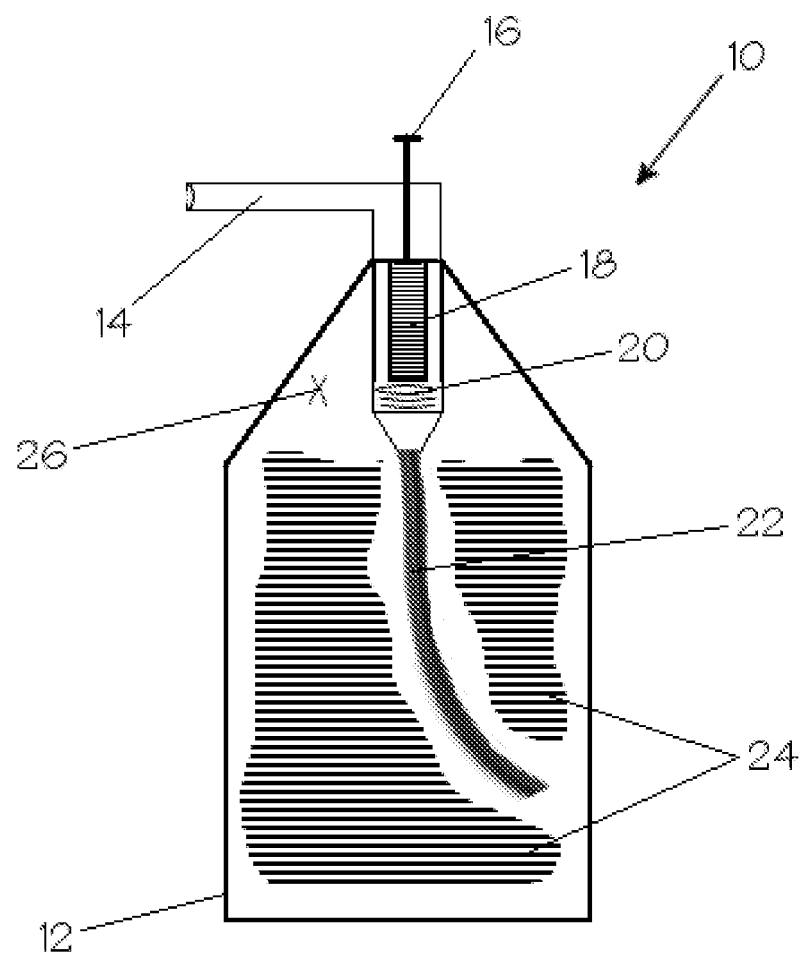
FIG. 4 is an illustration of the components of an exemplary device for delivery a dry dye formulation to the eye of a patient.

FIG. 4 provides an exemplary embodiment of one such delivery device 10. The delivery device 10 includes a hermetically sealed container 12 having a compressed gas 26 and a dry, powdered dye 24 contained therein. A tube 22 is disposed within sealed contained 12, tube 22 having an open end to receive compressed gas 26 and powdered dye 24 and direct the flow of the two to the valve assembly of the device. The valve assembly of delivery device 10 includes a chamber 28 in which valve 18 and spring 20 are disposed. A push button 16 is attached to the top of valve 18 and protrudes upwardly through a dispensing nozzle 14. As shown in FIG. 4, delivery device 10 is in a closed position. Spring 20 urges the top of valve 18 against the opening between chamber 28 and dispensing nozzle 14, thereby sealing the flow path between the two. The compressed gas 26 and powdered dye 24 are retained within sealed container 12. When a user of the delivery device 10 depresses push button 16, valve 18 is urged downward against spring 20. This opens the flow path between chamber 28 and dispensing nozzle 14, but does not close the flow path between chamber 28 and tube 22. Compressed gas 26, due to its compressed nature, flows through tube 22, passes through chamber 18, and passes out of dispensing nozzle 14. The compressed gas 26 acts as a carrier for dye 24, carrying it with it as it flows. Upon leaving container 12, dye 24 is deposited on a surface according to the orientation of dispensing tip 14. When the user releases push button 16, valve 18 is once again urged in an upward direction by spring 20, and the flow path from chamber 28 to dispensing nozzle 14 is closed.

It should be noted that in the embodiment of a delivery device shown in FIG. 4, the amount of dye delivered to a surface, such as the eye of a patient, is controlled directly by the user of the delivery device and is determined by the length of time over which the user depressed push button 16. In other embodiments, however, it is contemplated that a metering mechanism may be employed such that a single depression of push button 16 results in the delivery of a predetermined amount of dye 24. Such metering mechanisms are known in the art, and it is contemplated that any suitable metering mechanism may be used.

Likewise, devices for dispensing medicaments and other substances are known in the art. The present method is not limited to the use of any particular device for the delivery of the dye. Rather, any suitable device may be employed. In one embodiment of the invention dispensing devices maybe provided wherein the amount dispensed is predetermined by a manufacturer of the device, and the user of the dispensing device merely actuates the device to deliver the prescribed amount of dye. In all such cases, the present method avoids direct contact of a physical object with the eye of a patient.

Having thus described the preferred embodiment of the invention, what is claimed as new and desired to be protected by Letters Patent includes the following:

1. A method of staining an eye of a patient in need thereof with a powdered dye without contacting the surface of the eye with a physical object, the method comprising:
   (1) providing a delivery device comprising a sealed container, an actuator, a powdered dye within the sealed container, and a propellant under pressure within the sealed container; and
   (2) delivering the powdered dye to the surface of the eye by engaging the actuator to dispense the powdered dye from the delivery device,
   wherein the powdered dye is selected from the group consisting of Fluorescein, Lissamine Green, Rose Bengal, and combinations thereof; and
   the actuator is metered such that a single engagement of the actuator dispenses a predetermined amount of the powdered dye from the delivery device.

2. The method according to claim 1, wherein the predetermined amount of powdered dye dispensed from the delivery device is from about 0.001 mg to about 1 mg of the powdered dye.

3. The method according to claim 1, wherein the powdered dye is Fluorescein.

4. The method according to claim 1, wherein the powdered dye is Lissamine Green.

5. The method according to claim 1, wherein the powdered dye is Rose Bengal.

* * * * *